US007961085B2

(12) United States Patent
Almqvist et al.

(10) Patent No.: US 7,961,085 B2
(45) Date of Patent: Jun. 14, 2011

(54) METHOD TO MONITOR MANUAL STEERING OF DYNAMIC SYSTEMS AND DEVICE

(75) Inventors: Sven Almqvist, Trosa (SE); Klas Küntzel, Djursholm (SE)

(73) Assignee: AUTOLIV Development AB, Vargarda (SE)

( * ) Notice: Subject to any disclaimer, the term of this patent is extended or adjusted under 35 U.S.C. 154(b) by 308 days.

(21) Appl. No.: 12/293,425

(22) PCT Filed: Apr. 26, 2007

(86) PCT No.: PCT/SE2007/050280
§ 371 (c)(1),
(2), (4) Date: Dec. 23, 2008

(87) PCT Pub. No.: WO2007/136338
PCT Pub. Date: Nov. 29, 2007

(65) Prior Publication Data
US 2009/0273458 A1    Nov. 5, 2009

(30) Foreign Application Priority Data

May 23, 2006    (SE) ...................... 0601146

(51) Int. Cl.
*B60Q 1/00*    (2006.01)
(52) U.S. Cl. ..................... 340/439; 340/407.1; 340/438; 340/441
(58) Field of Classification Search .................. 340/439, 340/407.1, 7.6, 438, 441; 280/774; 434/62, 434/29, 69
See application file for complete search history.

(56) References Cited

U.S. PATENT DOCUMENTS

| | | | |
|---|---|---|---|
| 5,618,178 A * | 4/1997 | Copperman et al. | 434/62 |
| 5,719,561 A * | 2/1998 | Gonzales | 340/7.51 |
| 6,326,901 B1 * | 12/2001 | Gonzales | 340/7.2 |
| 6,793,234 B2 * | 9/2004 | Carlstedt et al. | 180/446 |
| 6,930,590 B2 * | 8/2005 | Ling et al. | 340/407.1 |
| 7,263,058 B2 * | 8/2007 | Joo | 370/203 |
| 7,283,056 B2 | 10/2007 | Bukman et al. | |
| 2003/0227374 A1 * | 12/2003 | Ling et al. | 340/407.1 |
| 2004/0054452 A1 * | 3/2004 | Bjorkman | 701/29 |
| 2004/0090321 A1 * | 5/2004 | Keutz | 340/438 |
| 2004/0252020 A1 * | 12/2004 | Matsumoto et al. | 340/438 |
| 2005/0065694 A1 * | 3/2005 | Nenninger | 701/70 |
| 2005/0127655 A1 * | 6/2005 | Muramatsu et al. | 280/774 |
| 2006/0241718 A1 * | 10/2006 | Tyler et al. | 607/45 |
| 2007/0181810 A1 * | 8/2007 | Tan et al. | 250/341.1 |
| 2007/0236450 A1 * | 10/2007 | Colgate et al. | 345/156 |
| 2008/0174415 A1 * | 7/2008 | Tanida et al. | 340/438 |
| 2008/0282437 A1 * | 11/2008 | Park | 2/1 |
| 2009/0326604 A1 * | 12/2009 | Tyler et al. | 607/45 |
| 2010/0188233 A1 * | 7/2010 | Kuntzel | 340/575 |

FOREIGN PATENT DOCUMENTS

WO    03/070504 A1    8/2003
WO    2005/059857 A1    6/2005

* cited by examiner

*Primary Examiner* — George A Bugg
*Assistant Examiner* — Hoi C Lau
(74) *Attorney, Agent, or Firm* — Young & Thompson

(57) ABSTRACT

The invention concerns a method and an arrangement for ensuring through active monitoring an attentive manual control of a dynamic system. The method and the arrangement use the tactile ability of the human hand to receive, particularly when the muscles are relaxed, certain types of vibrations through two sets of sensitive corpuscle in the human skin, known as the Meissner corpuscles and the Pacinian corpuscles, and the ability of the brain to provide an immediate response to these signals in the same interface to the object that the two sets of sensitive corpuscle are touching during the control and with immediate feedback from the control device of the dynamical system.

21 Claims, 2 Drawing Sheets

METHOD TO MONITOR MANUAL STEERING OF DYNAMIC SYSTEMS AND DEVICE

TECHNICAL AREA

The invention focuses on how manual control of a dynamic system, which may be a machine, a vehicle, a vessel, an aeroplane, construction plant, a construction machine, a military system, an instrument system, or any other dynamical system at all that is controlled manually by a person, should best be monitored with respect to the human factor, and which method is best suited to maintain and exploit human properties with respect to best responding in the person-machine interface to warning signals, such as may be caused by deficient control with respect to the control device.

The technical area of the invention can be given the title "active monitoring system" when the invention is applied to a motor vehicle as the controlled system. The application is valid as long as the control takes place with the aid of the human hand, whether this be directly or through amplifying and/or stabilising control systems.

THE PRIOR ART

Much interest has been directed for application within motor vehicles towards the task of eliminating dangers associated with deficient attentiveness at the steering wheel, something that may have various causes and expressions. The causes may include distraction in association with other activities such as a mobile telephone, radio or other sources of sound, or navigation, or other occupation. One central cause can be tiredness, which in the worst case may lead to a driver falling asleep at the steering wheel.

Several technical solutions are already known and many of these have been commercially realised, for example, measures that free the driver from undesired disturbances from mobile telephones and similar. In the event of distraction and deficient attentiveness or a growing tiredness of the driver when driving on a motorway, he or she can unintentionally come to exercise deficient steering wheel control such that the car wanders out into another lane. Cars are already available that are provided with systems that record deviations from the current lane and can use an alarm signal to warn the driver where the car is directed. Such systems may also initiate other protective mechanisms in the vehicle. Certain of these systems, however, require that the lines in the carriageway that define the lanes are visible, something that is not always possible.

One technical solution to reduce single-car accidents that are caused by inattentiveness, tiredness or falling asleep at the steering wheel and that has had a major influence on the accident rates in the US is that of providing the motorway with rumble strips, which cause a vibratory sound in the car if the wheels pass over the rumble strips.

The advantage of this method is its simplicity. The disadvantage here, however, as it is in the previously described method, is that the danger is discovered only when the faulty control has already had an effect on the position of the vehicle, and this may be too late.

It is also known to record the magnitude of the steering wheel angle and to record inactivity of the steering wheel, as a measure of the inattentiveness of the driver, as is that of recording the torque, and that of, described in the PCT application WO2005/059857, studying not only inactivity but also subsequent steering wheel motion and calculating in a computer programme the risks of inattentiveness as defined by the parameters, and to raise an alarm based on the calculation.

Other technically known solutions around the problem of tiredness have been directed at determining the eye movements and/or the eyelid movements of the driver, which are affected by different degrees of tiredness, and allowing such observations after processing to constitute the input signals to a warning and action system in the vehicle. Solutions of this nature, however, are technically advanced and may thus be prone to disturbance. The hand contact of the driver with the steering wheel and the locations of the hands around the steering wheel have formed the basis of some known methods in association with warning systems in motor vehicles.

Methods are known for motor vehicles that are based on regularly testing the speed of reaction, and in this way also the degree of awareness, of the driver. The German patent DE 19518914 describes an arrangement for testing the attentiveness and the reaction ability of the driver of a motor vehicle, which arrangement emits a signal, the reception of which must be confirmed by the driver by the pressing of a finger on the steering wheel. The patent descriptions in JP 4183439A1 and JP 5345569 cover the discovery and analysis of the contact of the driver with the steering wheel, in the first case with an arrangement that records an electrocardiogram with the subsequent analysis of the degree of awareness of the driver, and in the second case including the measurement of the forced applied to the steering wheel.

It is known from patent application US 20030189493 that sensors for determining that hand contact is taking place can be located in a certain specified manner around the circumference of the steering wheel, by the aid of which sensors the locations of the hands and the history of these locations can be analysed and compared with data from known accident statistics, etc. A method for measuring capacitively the contact between the hands of a driver and a steering wheel or other to control device is known from patent application US 20020170900.

BRIEF SUMMARY OF THE INVENTION

The present invention concerns a method for monitoring attentiveness during the manual control of a dynamic system, in which deficiencies of control are detected and warning signals are raised, and it is characterised in that the said warning signals are caused to be constituted by vibrations (w1) and (w2) in the physical-mechanical interface of the said system between the person and the machine (PM), where the vibrations are caused to have such frequencies, amplitudes and durations that the Meissner corpuscles (MC) and the Pacinian corpuscles (PC) on the inner surfaces of the hands and fingers are activated when the hand of the person comes into contact with the control device (W) for the control of the said system (V) and in that deficiencies in attentiveness are caused to be calculated on the basis of controlling movements of the said control device.

DESCRIPTION OF THE INVENTION

The present invention differs from known methods and systems of devices in that it sends signals, which have been determined on a medical-technical basis, directly to the human brain through two types of specified sensitive corpuscle in the hands in a particularly efficient, recognisable and pleasant manner, as soon as a normal control pattern disappears.

The invention is based upon and combines the effects of four known facts. [1] It is known within medicine that the skin of the inner hand and fingers of humans is provided with several types of sensitive corpuscles, two of which, the Meissner corpuscles and the Pacinian corpuscles, have the ability to emit very rapid and strong impulses to the brain when they are stimulated by vibrations of certain frequencies, amplitudes and durations. [2] It is also known within medicine how the brain works with increasing tiredness, falling asleep, and waking up. Thus, it is known that sleep is a natural process in the human brain that occurs instantaneously after a period of relaxation, and that all conscious muscle motion controlled by the person ceases once the person is asleep. Furthermore, it is known that a transition from sleep to an awake and conscious state in the brain can also take place instantaneously when an external disturbance of sufficient intensity and nature arrives, naturally under the condition that the person involved is healthy and not under the influence of drugs, alcohol or other agent. [3] It is furthermore generally known that the sensitivity of the hands is actively involved during manual control in which the hands are in contact with a control device. [4] Finally, we know that so control of several groups of dynamic systems normally requires many small corrections and control impulses that follow each other closely in time. Dynamical systems can be subject to external disturbances. The dynamic properties of the system depend on a number of physical parameters of the controlled system, of the control system itself, and of the nature of the disturbances. In the case of motor vehicles, which the inventors have studied in detail, the dynamical properties of the vehicle are in general of such a nature that small corrections using steering wheel motion, closely spaced in time, constitute a normal control behaviour required to maintain the vehicle in the desired lane when driving along a motorway.

The present invention has latched onto these four facts and it defines a method and a system that monitor the motion of the control device and in the event of deficient control raise alarm signals in the form of recognisable bursts of vibrations, that are particularly well recognised by two specified sensitive organs in the skin of the inner hand and fingers, particularly in the case of a relaxed grip on the steering wheel. The invention opens in this way the most rapid and most secure pathway for warning signals to the brain of the controlling person, and this leads to the most rapid instinctive reaction from the brain, in that this reaction goes to the same part of the body from which the alarm signal arrived. Thus, the invention differs from other hitherto known methods not only in the security of the alarm signals, but also in the speed of reaction in the response to the signals. The invention provides the opportunity for individual adaptation and the setting of the parameters of the nature and levels of the alarm signals. A system according to the invention can be readily integrated with other systems in a motor vehicle or in any other dynamic system.

DESCRIPTION OF THE PROBLEM

During the manual control of a dynamic system, such as a vehicle, a vessel or any other controlled system, one or both hands are in contact with a control device, which may be a steering wheel, joystick, a rudder, or similar. The steering wheel of a vehicle will be discussed in the description below for the purposes of simplicity, but the description and the invention can concern in applicable parts other types of control device and other types of risk-filled situations than those described. The steering wheel constitutes the continuous person-machine interface when driving a vehicle, while the accelerator pedal, brake pedal, gear lever and other controls constitute discontinuous interfaces. Management of the steering wheel is, together with management of the accelerator and brake, the vital task that the driver continuously must give his or her attention to while driving, as long as vehicle technology is based on manual control. The actual control task is, as is all human activity, subordinate to the brain, even if the brain does obtain aid from pre-programmed nerve systems in which motor patterns and other patterns of action have been stored and can be used. In its non-tired, non-influenced and healthy condition, the brain is capable of managing to control a motor vehicle even in difficult traffic situations. The brain receives, interprets and co-ordinates impulses based on incoming signals with the aid of the five senses: sight, hearing, feeling, smell and taste. During the actual task of driving, the primary senses are those of sight and hearing, and that of feeling in, primarily, the hands, but also sensation in other parts of the body, with the help of which such factors as acceleration, braking, road camber and lateral acceleration can be determined. The tasks of the eyes and sight are central in road safety. It is known that a so driver often moves the point of vision in the normal case to the edges of the road and to crossing roads, and it is known that a distracted or tired driver tends to hold the point of vision more stationary and directed straight forwards on the road, obtaining in this way an impaired ability to discover traffic hazards from the side, for example at road junctions. It is also known that increasing tiredness often entails muscle relaxation, which occurs regularly when falling asleep. Relaxation of a car driver may lead to a softer hand grip and the hands falling into a resting position. A further known consequence is that steering wheel motions occur more seldom and with a greater magnitude, and this has the consequence that the pathway of travel of the car becomes more crooked. When the driver has fully fallen asleep, the hands may be resting without force on the steering wheel or, in the worst case, may have fully released the steering wheel. It is particularly important to consider driving on a motorway at high speeds in this context. It is known that the risk of losing attentiveness increases during monotonous driving for a long period when tired, and it is known that the risk of an accident increases with increasing speed. For this reason we will consider as a part of the description of the problem, a driver who is driving a motor vehicle at normal speed on a motorway. It is assumed that the speed lies between 90 and 150 km/hour, depending on the local speed restrictions. Let us now consider a tired driver at the steering wheel: the situation may arise in which the driver starts to fall asleep, the muscles start to relax and sleep approaches, such that the number of steering wheel movements per unit of time gradually becomes lower, and finally becomes zero when sleep arrives. If we further consider that the car's cruise-control system has been engaged or that the position of the accelerator pedal is not changed, then we have a situation in which it is a matter of seconds available in which to prevent a serious accident. The car will move 25-42 meters in one second at the specified range of speeds, 250-420 meters in 10 seconds. A very rapidly active method is required in order to prevent a fatal traffic accident in this situation, something that the present invention offers.

THE SOLUTION

The method according to the present invention uses the person-machine interface not only for the detection of deficiency of control through the registration of the motion of the control device, but also for the awakening of attentiveness through warning signals to the human brain from the so called Meissner corpuscles and the Pacinian corpuscles in the skin of the inner hand and fingers of a person when in contact with the control device, and through the recording within a fraction of a second of the direct response in the same interface, and—should a response be lacking—initiating continued measures for awakening attentiveness and increasing safety in order to prevent or reduce the effects of deficient control. The rapidity of a method according to the invention is based upon several interacting factors. Medical research has shown that the human brain experiences vibrations in the inner skin of the hands and fingers more rapidly than any other sensory input. This ability of the brain to experience sensory input is influenced by, among other factors, the age of the individual, the temperature of the hands during the input, and whether the individual has been working with vibrating tools immediately before the input. According to this method, the warning signal to the driver in the person-machine interface is given directly to the brain and does not require any interpretation, since it is derived directly from the person-machine interface and thus it is directly coupled with the control task. Two conclusions can be drawn from a direct response in less than a second in the form of steering wheel motion: that the driver has his or her hands still in contact with the steering wheel when the warning signal arrives, and that he or she has experienced the sensation of feeling and has thus been awakened from sleep and regained control of the steering wheel. The first reaction will be, apart from that of regaining the function of memory and experience of sight, which gives an increased insight into the situation, that of steering wheel motion, which is not only instinctive, since the warning arises in the contact of the hand with the steering wheel, but also conscious, since the brain has been awakened to consciousness. The invention thus exploits the person-machine interface both for the task of detecting deficiencies in control and for the task of drawing the attention of the person in control to the control task. It is here that the fundamental reason for the rapidity and simplicity of the method lies. Allowing the length of the period without steering wheel motion to form the basis of the alarm in the event of deficiencies in control, as is done in the case of the motor vehicle, is one of the basic ideas of the invention. This idea has been confirmed through studies and practical experiments that the inventors have had carried out. The experiments have taken place, in particular, during normal driving on a motorway, whereby the frequency and the rhythm of steering wheel motion has been studied, in particular, the interval between conscious steering wheel movements. The experiments show that it is a matter of small corrections, which normally appear after a period that is typically one second or a few seconds. Experiments carried out with different drivers have shown an average of slightly more than 32-78 steering wheel movements per minute, or 0.5-1.2 steering wheel movements per second, within the area of variation 20-80 steering wheel movements per minute. The observations have been taken during a period of one minute at a time, during which the number of conscious steering wheel movements has been calculated, where each movement of the steering wheel after a stationary condition of the steering wheel has been counted as one steering wheel movement, independently of its direction and of its magnitude. The movements do not take place at a constant frequency: they often occur in groups of 2-3 movements, more frequently during, for example, overtaking or new traffic situations. However, even during calm, monotonous and uninterrupted driving on a motorway in a straight line, steering wheel movements arise in order to carry out small corrections, normally within a period of 1-4 seconds after the previous steering wheel movement. The steering wheel movements arise more seldom, with a longer time between them, when attentiveness is at a low level as is the case for a tired driver, and they may have a larger amplitude, probably in order to be able to correct an error in the direction of driving that has already arisen. In order, furthermore, to include the increased risk of an accident at high speed, the method according to the invention includes allowing the stretch of road traversed since the most recent steering wheel movement to determine the raising of the alarm. The lack of a direct response suggests that a dangerous situation has arisen: either the hands of the driver have already lost contact with the steering wheel, or unconsciousness is so deep that not even the vibrations of the steering wheel specified according to the invention are sufficient to break it. The method and the system according to the invention allow in this situation that the alarm signal is increased and that other known systems for active safety are initiated, such as known methods for external and internal signalling, automatic intervention in the progress of the vehicle, and similar methods.

A system according to the invention comprises in the case of a motor vehicle at least the following parts: means for detecting conscious steering wheel movements, means for calculating the stretch of road traversed since the most recent conscious steering wheel movement, means for controlling the raising of an alarm signal following the requirements specified by the method, means for performing mechanical vibrations in the control device, the steering wheel, in accordance with these requirements, on surfaces that are in contact with the hands of the driver when driving and in that manner that the method defines, and means for such integration with other systems in the vehicle that are considered to be necessary and suitable. It may be appropriate that the operating conditions of the system and any alarms that it raises are recorded in the on-board computer and/or the tachograph.

ADVANTAGES

The present invention provides more rapidly and more securely than any other known method or known system the function of awakening a person to attentiveness during manual control by directly sending an alarm to the brain through the hands, which are involved with the control task, in the most efficient, recognisable and pleasant manner by using two of the vibration-sensitive sensitive corpuscles in the skin and by immediately recording the response from the brain to the same part of the body at which the sensitive corpuscles that are emitting signals are located, which process is very similar to the instinctive reaction to a sensation of pain or a lower level of sensation of feeling. Through allowing the feedback from the controlled system to be based on the motion of the control device, as is done according to the method, rather than on the motion of the vehicle, the time delay and the phase displacement, which otherwise would affect the feedback, is removed, and the rapidity of the method thus increases. An additional advantage of a method according to the invention is its simplicity, which also has a positive effect on its security and reliability.

DESCRIPTION OF A HERE SUGGESTED EMBODIMENT

The method, the system and the arrangements according to one embodiment of the invention will be described below with reference to the drawings listed above. In order to set the invention into its correct context, the connections within a manually controlled system are shown in principle in FIG. 1 with dashed lines, and an additional monitoring system according to the invention with full lines:

D denotes the person in control, "Driver"
H denotes this person's hand, "Hand"
W denotes the control device, "steering wheel"
PM denotes the physical-mechanical person-machine interface, "physical mechanical border"
V denotes the controlled system, "vehicle"
E denotes the surroundings of the controlled system, "environment"
S denotes the senses, "senses"
I denotes instruments, "instruments"
f1 denotes the movements of the controlled system that can be detected, "feedback 1"
f2 denotes the situation of the surroundings that can be detected, "feedback 2"
f3 denotes the instrument data, "feedback 3"

Figure 1:
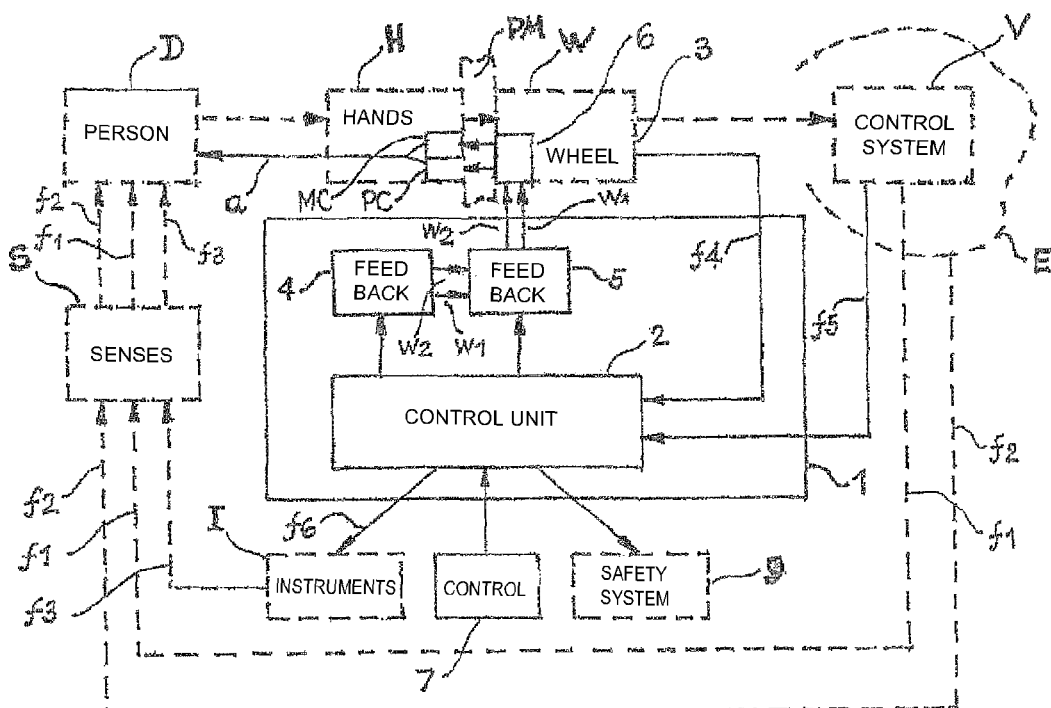
FIG. 1 shows a schematic block diagram of the manual control of a dynamic system with the addition of a monitoring system 1 according to the invention.

As it is intended that the arrows in FIG. 1 should show, the controlling person D performs controlling movements with the control device W using the hands H, which control device controls the system V. Feedback occurs through the controlling person D experiencing the behaviour f1 of the controlled system V through his or her senses S, observing the surroundings E through f2, and reading the instruments I through f3. When applied to the case of a motor vehicle, the controlling to person D is the driver, the control device W is the steering wheel, the controlled system V is the motor vehicle, and the surroundings E are the traffic situation. In association with the monitoring system according to the invention, the following symbols have been added to the drawing:

1 denotes a monitoring system according to the invention
2 denotes a control unit with electronic circuits in the monitoring system
3 denotes sensors at or in the control device
4 denotes oscillators and their driving circuits
5 denotes amplifiers and mixers
6 denotes vibrators in the control device
w1 denotes warning signals to MC, "warning signal I"
w2 denotes warning signals to PC, "warning signal 2"
MC denotes Meissner corpuscles in the hand, "Meissner corpuscle"
PC denotes Pacinian corpuscles in the hand, "Pacinian corpuscle"
a denotes signals from MC+PC along nerve pathways, "alert signal"
f4 denotes signals from sensors at the control device, "feedback 4"
f5 denotes selected data from the controlled system, "feedback 5"
f6 denotes selected data from the monitoring system, "feedback 6"
9 denotes the active safety systems of the vehicle
10 denotes the on-board computer of the vehicle and/or the tachograph of the vehicle.

The auxiliary monitoring system 1 has the following function: According to the invention, the system notes deficiencies in the control principally through deficiencies in the movements f4 of the control device W. When these deficiencies have been present along a certain recorded stretch of travel, according to the method of the invention, the system 1 generates warning signals w1 and w2 on certain pre-programmed and adjustable conditions through at least one burst of recognisable vibrations of such a strength and nature in the person-machine interface PM that they are readily detected by two types of sensitive corpuscle MC and PC in the skin surface of the inner surface of the hand and the fingers, which rest in contact with the control device W, the vibrations being of such a nature, frequency, amplitude and duration that an evident impulse a is led in an upwards direction along the nerve pathways to the brain, and wakes the brain to consciousness. According to the invention, deficiencies in control are detected primarily through measured values from a sensor 3 that records, f4, each intentional controlling movement greater than approximately 0.5 degree, independently of its direction, directly in association with the control device W. The sensor 3 transmits a signal, f4, on each occasion on which such a steering wheel movement takes place to a control unit 2 that contains logic circuits. In the case of a motor vehicle, the control unit in the vehicle V collects the instantaneous growth f5 of the stretch of travel, which is added in a counter in the control unit after the most recent steering wheel movement. The sensor 3 transmits a signal f4 to the control unit 2 that resets this counter to zero on every steering wheel movement that is carried out. Should such a signal not arrive along a stretch of travel following the most recent steering wheel movement that amounts to a threshold value that is stored in the control unit 2 and that can be set by the use of certain controls 7, this is then, according to the invention, a reliable measure of deficient control. When the counter has reached such a pre-programmed threshold value, the control unit sends a starting impulse to the driving circuits 4, 5 of the vibrators 6, which circuits work to a program that is stored in the control unit 2. It is appropriate that the monitoring system have a manual setting arrangement 7, with the aid of which vibration amplitudes, threshold values and other parameters can be set. Furthermore, the system can transmit further signals f6 to the driver, such as sound or light signals, information about status, the level of alarm and the values that have been set, including signals to the instrument panel or display I. The operational status and the alarms of the monitoring system can be recorded in the on-board computer or tachograph 10 and its connection and disconnection can be controlled by the speed of the vehicle. It may have a block, depending on traffic regulations, against manual disconnection. In the case of application to a vehicle, a burst of vibrations at least of type w1 or type w2 and preferably both w1 and w2 at the same time and preferably a recognisable sequence of bursts is to lead to the driver immediately regaining control. If this occurs, the counter in the control unit 2 is reset to zero after receiving a signal f4 from 3, after which the control unit 2 transmits a stop signal to the alarm circuits 4, such that the production of the signal ceases. If control is not regained, such that no signals are emitted from the sensor 3, the value in the counter of the control unit 2 continues to increase, whereby the control unit may be programmed first to increase the amplitude of w1 and w2 and subsequently to activate known safety systems 9 in the vehicle. Historical alarm data can be stored in the on-board computer or tachograph if this is required. The monitoring system 1 and its control unit 2 and the associated circuits are here described for the sake of clarity as a separate system with separate parts in association with the present invention, but it lies within the scope of the invention and within the nature of things that its functions and units can be integrated in a controlled system, such as a motor vehicle, in a manner that is both functional, economic and advantageous from the point of view of production, with other electronic circuits, such as an on-board computer, tachograph, instrumentation, cabling and other components of the vehicle. Deficient attentiveness is defined according to the method of the invention as the duration of a cessation of steering wheel movements measured in terms of the stretch f5 of road traversed following the most recent steering wheel movement. If only the time of the duration of cessation of steering wheel movement were counted, the method and the system would not take into consideration the major influence on the risk of an accident and on the consequences of an accident that the actual speed of travel has. Attentiveness is recorded as each little conscious steering wheel movement f4, which thus resets to zero a counter in the control unit 2, which counter measures the stretch of travel after the most recent steering wheel movement. The register is reset to zero also at each speed that is less than, for example 50 km/hour, which in such a case means that the monitoring system is intended to function at speeds that exceed 50 km/hour. The instantaneous value of the register thus constitutes a measure of the duration of deficient attentiveness, relative to the consequences. Different levels of alarm can be selected and stored in the calculating circuits 2 of the monitoring system, in the form of defined threshold values that cause the raising of different amplitudes of alarm, and, as a final resort, measures 9 to prevent accidents. If the selected and adjustable threshold values are selected, for example, to be 200, 300 and 400 meters, then they would correspond to time intervals of 6.5, 9.8 and 13 seconds, respectively, at a speed of 110 km/hour. The sensor 3 for detecting steering wheel movement can be of different types and designs and it may be based on known technology for the measurement of position, angle or movement carried out, such that in a robust and reliable manner with sufficient precision can detect each conscious controlling movement of the control device and such that effects of other disturbing factors, bumps in the road or vibrations can be filtered out using known technology. Vibrators 6 according to the invention can be of any known type at all. Oscillating mechanical vibrators can be selected that are electromagnetically excited and that are fed from one or more power stages 5 with or without mixers, which in turn are fed from, preferably, two oscillator circuits 4 through amplifiers 5 and they may be controlled by the control unit 2 with respect not only to the alarm programme, such as its starting and stopping, duration, pauses and amplitude programme, but also parameters that are fed in, such as settings for frequency and volume. The frequencies of the signals w1 and w2 are generated in the relevant oscillator circuits 4 and they pass through the amplifier circuits 5 with or without mixers and separate power stages. In the case that has been described, the induced vibrations arise with both frequencies at the same time in a common type of vibrator. It is an alternative that separate vibrators are used for the two frequency ranges. The amplitudes are automatically controlled according to the alarm programme that has been fed into the control unit, the parameters of which can be set manually by the unit 7. The setting of certain frequency ranges can be carried out in the same manner, for example 20-40 Hz and 200-300 Hz at the same time.

According to one design, the vibrations are caused to recur after a certain predetermined time after a deficiency in control has occurred. The recurrence can, for example, take place 15 minutes afterwards, in order to prevent a repeat occurrence of sleeping at the steering wheel.

Figure 2:
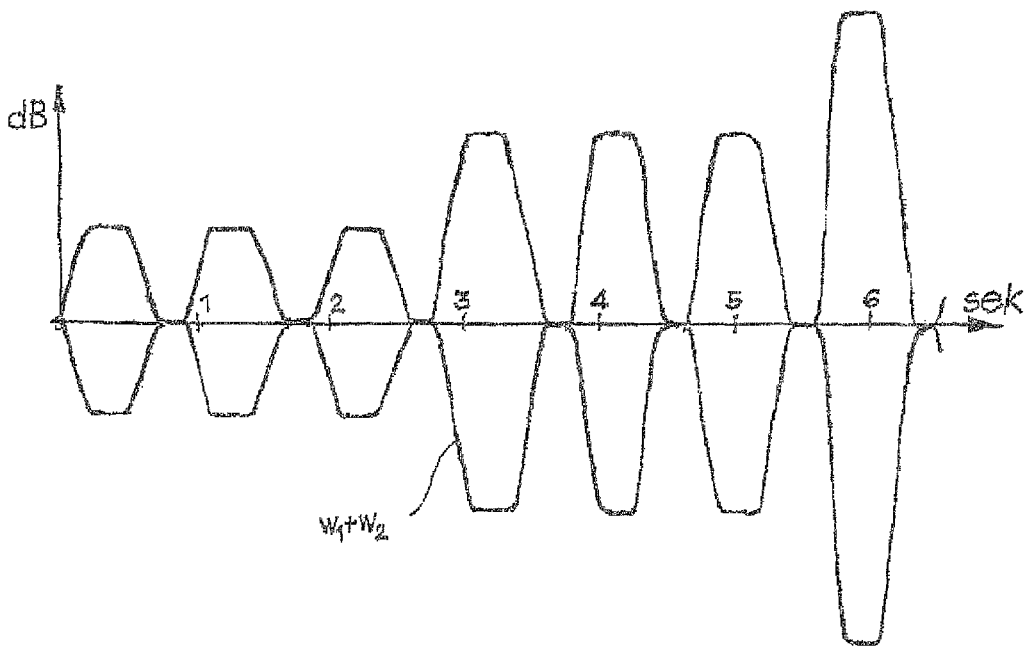
FIG. 2 shows the envelope of vibration bursts according to the invention.

The alarm design that is exemplified in FIG. 2 is controlled by programs in the control unit 2, the parameters of which can be preset using the unit 7. FIG. 2 gives examples of a suitable design for the vibration signals w1 and w2 according to the method of the invention to trigger the person who is carrying out the manual control. The curve in the drawing constitutes the envelope of the amplitude of the vibration bursts. The signal frequencies that give the greatest effect on the Meissner corpuscles and the Pacinian corpuscles are approximately 30 Hz and 250 Hz, respectively, and they should be given in a recognisable sequence of bursts of the same or of differing durations of 250-750 msec, followed by pauses of duration of at least 150 msec, and with sequentially increasing amplitudes, as suggested by the drawing. The method and the system comprise the wakening of the immediate attentiveness of the driver by sending tactile warning signals w1 and w2 to, principally, two specially specified sets of sensitive corpuscle in the skin of the inner hand and the fingers. The lengths of the bursts may follow a selected pattern, a Morse code signal, for example, in order to obtain increased ease of recognition. All desired levels of alarm may be selected within the scope of the invention, and the invention is not bound to some values of alarm level as a measure of deficient attentiveness. There may be several reasons for the desire to set individual values for the amplitudes of the alarms in the system. The threshold values for the reaction of the sensitive corpuscles to vibrations increases with increasing age and with decreasing skin temperature and can vary between individuals.

It lies within the scope of one skilled in the arts to be able to set a suitable individual level for the vibrations.

Figure 3:
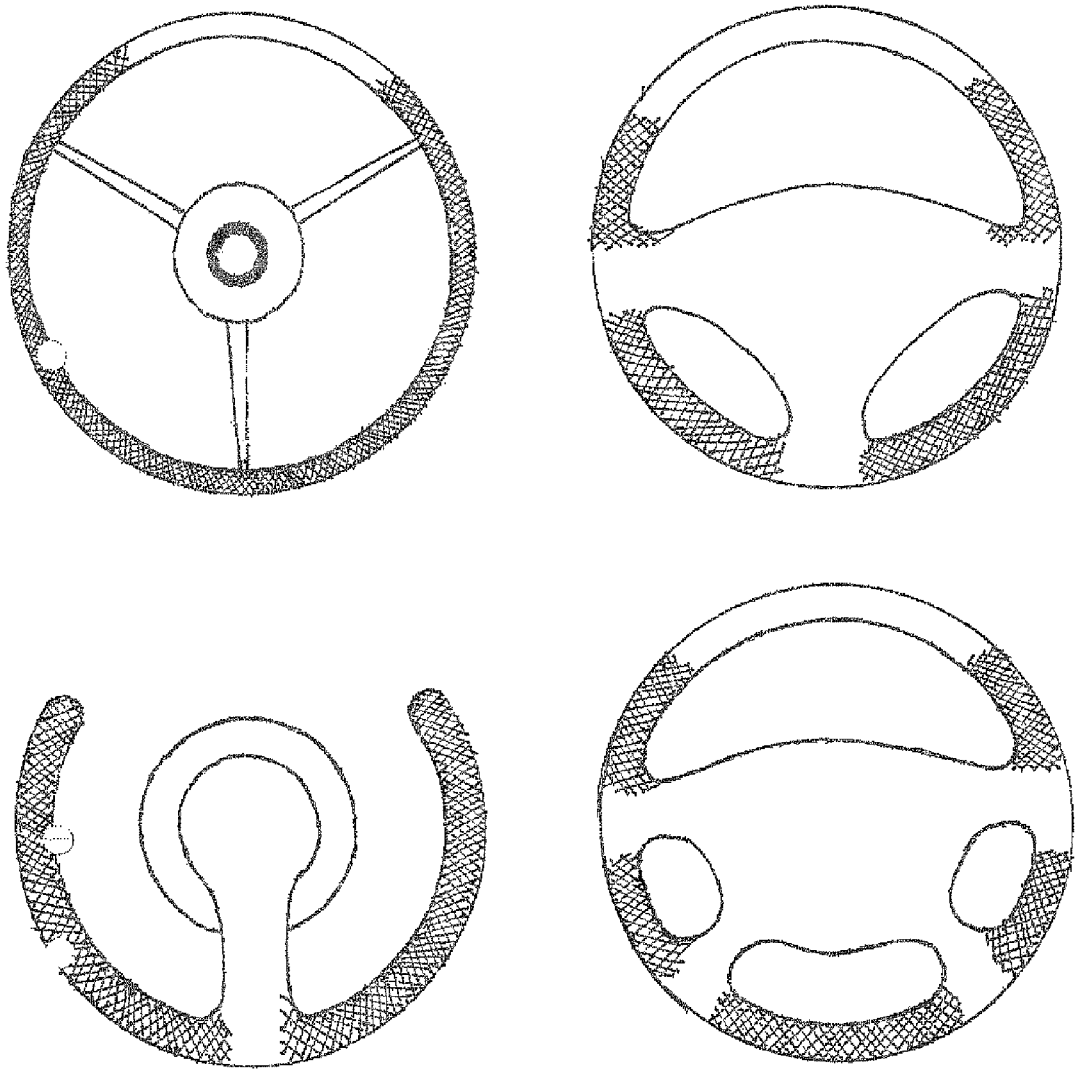
FIG. 3 shows examples of the locations of steering wheel vibrators 6 according to the invention.

FIG. 3 provides examples of the location of steering wheel vibrators in steering wheels of various designs. The hatched to areas around the circumference of the steering wheel have been indicated as possible locations, where the hands of a driver often rest and where they can be expected to rest in relaxed situations. The location is, according to the invention, not restricted to the positions suggested: they can be selected in each individual case such that the vibrations reach the inner surfaces of the hand and/or the fingers, when the hand grips or rests on the steering wheel. It is preferable that steering wheel vibrators according to the invention are integrated into the design of the steering wheel, but they may also be manufactured for external mounting onto a steering wheel.

The present invention for the monitoring of manual control of dynamical system has been described in detail for an application concerning the control of motor vehicles, which application can be realised in different manners, but it is not limited to the embodiments described here and in the drawings since it can be varied within the scope of the attached patent claims.

The invention claimed is:

1. A method for monitoring attentiveness during a manual control of a dynamic system, comprising:
    detecting deficiencies of control; and
    emitting warning signals,
    wherein said warning signals are caused to be constituted by a pair of vibrations of different frequencies (w1, w2) in a surface of a steering wheel of a vehicle from oscillators arranged in or on the steering wheel in a physical-mechanical interface of said system between the person and a machine (PM), where the vibrations are caused to have such frequencies, amplitudes and durations that a Meissner corpuscles (MC) and a Pacinian corpuscles (PC) on inner surfaces of hands and fingers are activated when the hand of the person comes into contact with a control device (W) for the control of said system (V) and deficiencies in attentiveness are caused to trigger said vibrations and said vibration frequencies of said pair of vibrations (w1, w2) lie in the interval 1-150 Hz and 150-500 Hz respectively.

2. The method according to claim 1, further comprising:
    detecting, via an electronic circuit, when the deficiency in control of the person has ceased.

3. The method according to claim 1, wherein said pair of vibrations (w1, w2) are caused to occur for a duration of approximately 700 msec between pauses of at least 150 msec duration.

4. The method according to claim 3, wherein upon the deficiencies in control of the person failing to cease on the activation of said vibrations, further vibrations with higher amplitude are caused to be activated.

5. The method according to claim 1, wherein said vibrations (w1); (w2) are caused to cease when the deficiencies in control of the person have ceased.

6. The method according to claim 1, wherein said amplitudes of said pair of vibrations (w1, w2) are caused to be selected at least one of manually and automatically, at a level below a threshold.

7. The method according to claim 1, wherein the controlled dynamical system is a motor vehicle, and at least one of time and stretch of travel traversed after a most recent recorded movement of the control device is caused to constitute a measure of deficient control.

8. An arrangement for monitoring attentiveness during a manual control of a dynamic system, in which deficiencies of control are detected and warning signals are emitted, comprising:
driving circuits (4, 5); and
vibrators (6) are present arranged to generate said warning signals of a steering wheel from oscillators arranged in or on the steering wheel in a physical-mechanical interface of said system between a person and a machine (PM),
wherein said driving circuits (4, 5) are arranged to generate vibrations with frequencies, amplitudes and durations that activate a Meissner corpuscles (MC) and a Pacinian corpuscles (PC), respectively, on an inner surfaces of the hands and fingers when a hand of the person comes into contact with a control device (W) controlling said system (V) and in that an electronic circuit (2) is arranged to calculate deficiencies in attentiveness and in that the frequencies (w1,w2) of said vibrations lie within the interval 1-150 Hz and 150-500 Hz respectively.

9. The arrangement according to claim 8, further comprising:
an electronic circuit (2) arranged to detect when the deficiency in control of the person has ceased.

10. The arrangement according to claim 8, wherein said driving circuits and said vibrators (4, 5, 6) are arranged to control said vibrators with the frequencies 30 Hz and 250 Hz.

11. The arrangement according to claim 9, wherein said driving circuits and said vibrators (4, 5, 6) are arranged to control said vibrators at the same time.

12. The arrangement according to claim 10, wherein said driving circuits and said vibrators (4, 5, 6) are arranged to generate said pair of vibrations (w1, w2) in bursts with a duration of one second at the most and with intermediate pauses of a duration of at least 150 msec.

13. The arrangement according to claim 8, wherein said driving circuits and said vibrators (4, 5, 6) are arranged such that they can be manually set with respect to a mixture of said pair of vibrations (w1, w2), the frequencies, amplitudes, and durations, and in that said driving circuits and said vibrators (4, 5, 6) are arranged to generate said pair of vibrations (w1, w2) with increasing amplitudes while remaining under a threshold.

14. The arrangement according to claim 8, wherein the arrangement comprises a control unit (2) arranged to control the start of said driving circuits and said vibrators (4, 5, 6) for generating said pair of vibrations (w1, w2) and comprising logic circuits (2) arranged to detect a deficient control, in that during operation of the vehicle said circuits are arranged to update stretch of road traversed following a most recent movement of said control device on the basis of signals (f4) from a sensor (3) of steering wheel movement.

15. The arrangement according to claim 8, wherein said vibrations are caused to restart after a certain pre-determined interval.

16. The method according to claim 2, wherein said vibrations (w1); (w2) are caused to occur for a duration of approximately 700 msec between pauses of at least 150 msec duration.

17. The method according to claim 2, wherein said pair of vibrations (w1, w2) are caused to cease when the deficiencies in control of the person have ceased.

18. The method according to claim 3, wherein said pair of vibrations (w1, w2) are caused to cease when the deficiencies in control of the person have ceased.

19. The method according to claim 4, wherein said pair of vibrations (w1, w2) are caused to cease when the deficiencies in control of the person have ceased.

20. The method according to claim 2, wherein said amplitudes of said pair of vibrations (w1, w2) are caused to be selected at least one of manually and automatically, at a level below a threshold.

21. The method according to claim 1, wherein said vibration frequencies (w1, w2) are 30 Hz and 250 Hz respectively.

* * * * *